(12) United States Patent
Heinz et al.

(10) Patent No.: US 7,887,849 B2
(45) Date of Patent: Feb. 15, 2011

(54) PIGMENT MIXTURE

(75) Inventors: Dieter Heinz, Heppenheim (DE); Ralf Anselmann, Luedinghausen-Seppenrade (DE); Klaus Boehm, Rossdorf (DE); Sabine Schoen, Herten (DE)

(73) Assignee: Merck Patent GmbH, Darmstadt (DE)

( * ) Notice: Subject to any disclaimer, the term of this patent is extended or adjusted under 35 U.S.C. 154(b) by 823 days.

(21) Appl. No.: 11/631,183

(22) PCT Filed: Jun. 30, 2005

(86) PCT No.: PCT/EP2005/007036

§ 371 (c)(1),
(2), (4) Date: Dec. 29, 2006

(87) PCT Pub. No.: WO2006/002911

PCT Pub. Date: Jan. 12, 2006

(65) Prior Publication Data

US 2008/0305184 A1  Dec. 11, 2008

(30) Foreign Application Priority Data

Jul. 1, 2004 (DE) .................. 10 2004 032 121

(51) Int. Cl.
| | | |
|---|---|---|
| A61K 8/19 | (2006.01) | |
| A61K 8/25 | (2006.01) | |
| C04B 14/34 | (2006.01) | |
| C04B 14/22 | (2006.01) | |
| C04B 14/20 | (2006.01) | |
| C09C 3/06 | (2006.01) | |
| C09D 11/02 | (2006.01) | |
| C09D 11/00 | (2006.01) | |

(52) U.S. Cl. .................. 424/646; 106/479; 106/489; 106/436; 106/457; 106/483; 106/417; 106/31.9; 424/653; 424/724

(58) Field of Classification Search .................. None
See application file for complete search history.

(56) References Cited

U.S. PATENT DOCUMENTS

| | | |
|---|---|---|
| 6,162,374 A | 12/2000 | Schoen et al. |
| 6,517,628 B1 | 2/2003 | Pfaff et al. |
| 6,632,275 B1 | 10/2003 | Schoen et al. |
| 6,743,285 B1 * | 6/2004 | Anselmann et al. ......... 106/415 |
| 7,172,803 B2 * | 2/2007 | Raupach et al. ............. 428/198 |
| 2002/0120051 A1 * | 8/2002 | Brehm et al. ................ 524/494 |
| 2004/0191198 A1 | 9/2004 | Hochstein et al. |

FOREIGN PATENT DOCUMENTS

| | | | |
|---|---|---|---|
| EP | 1013723 | * | 6/2000 |
| WO | WO2004/012515 | * | 2/2004 |
| WO | 2004/061012 A | | 7/2004 |

* cited by examiner

*Primary Examiner*—Shanon A Foley
(74) *Attorney, Agent, or Firm*—Millen, White, Zelano & Branigan, P.C.

(57) ABSTRACT

The invention relates to a pigment mixture consisting of at least two constituents, constituent A being uncoated, monocoated or multicoated glass lamellae, and constituent B being nacreous pigments based on phyllosilicates, $SiO_2$ lamellae, $Fe_2O_3$ lamellae or $Al_2O_3$ lamellae. The invention also relates to the use of said pigment mixture, inter alia, in paints, dyes, especially printing inks, plastics, powder paints, pastes and cosmetic formulations.

20 Claims, No Drawings

PIGMENT MIXTURE

The present invention relates to a pigment mixture consisting of at least two components, where component A comprises uncoated or mono- or polycoated glass flakes and component B comprises coated or uncoated BiOCl pigments or pearlescent pigments based on phyllosilicates, $SiO_2$ flakes, $Fe_2O_3$ flakes or $Al_2O_3$ flakes, and to the use thereof, inter alia, in surface coatings, inks, plastics, powder coatings, ceramic glazes, plastic films and cosmetic formulations.

Pearlescent pigments are thin flakes of a colourless or coloured transparent or semitransparent material. Pearlescent pigments based on mica flakes have been known for more than 30 years.

Pearlescent pigments based on glass flakes have much higher gloss and significantly higher brightness than pearlescent pigments based on mica. The reason for this is that the glass flakes have a better plane-parallel surface, which is necessary for reflection.

This advantage of the significantly greater gloss and glitter effect is frequently countered by disadvantages in processability. Thus, glass flakes cannot be printed as simply as pearlescent pigments based on mica. The use of effect pigments based on mica in printing is described, for example, in "Effektpigmente für die Druckindustrie—Vom Design zum Druck—" [Effect Pigments for the Printing Industry—From Design to Print—] by Merck KGaA, published September 2003. In automobile paints comprising glass flakes, the applicational properties are impaired, such as, for example, DOI (=depth of image) or fisheye test. On incorporation of glass flakes into plastics, the abrasive properties are also striking in addition to the flow lines.

The object of the present invention is to increase the processability of glass flakes, in particular in industrial applications.

Surprisingly, it has now been found that the advantageous applicational properties of commercial pearlescent pigments based on mica, $SiO_2$ or $Al_2O_3$ can be combined with the good gloss and glitter properties of pearlescent pigments based on glass flakes if coated or uncoated glass flakes are admixed with conventional pearlescent pigments.

The mixing of pearlescent pigments based on various base substrates gives rise to an unexpected synergy effect, which provides the application systems with high gloss and at the same time significantly increases the processability of the glass flakes. The pigment mixture according to the invention is distinguished by very strong glittering and high brightness, can be incorporated very well into the various application media and achieves excellent hiding power.

The mixing ratio of component A and component B is preferably 10:90 to 50:50. Preferred mixtures comprise components A and B in the ratio 10:90, 20:80, 25:75, 30:70, 40:60 and 50:50. Component A is pre-sent in the pigment mixture according to the invention in a maximum amount of 50% by weight.

The present invention thus relates to a pigment mixture consisting of at least two components, where component A comprises uncoated or mono- or polycoated glass flakes and component B comprises coated or uncoated BiOCl pigments and/or pearlescent pigments based on phyllosilicates, $SiO_2$ flakes, $Fe_2O_3$ flakes or $Al_2O_3$ flakes.

The invention likewise relates to the formulations which comprise the pigment mixture according to the invention.

As essential constituent, the pigment mixture according to the invention comprises glass flakes. The glass flakes are preferably completely or partly covered with one or more layers of metal oxides, metal sulfides, metal oxynitrides, metal suboxides, metals and mixtures thereof.

Suitable pearlescent pigments based on coated glass flakes are known, for example, from WO 97/46624, WO 02/090448 A2 and WO 03/006558 A2.

The thickness of the glass flakes is preferably $\leq 1$ µm, in particular $\leq 0.9$ µm and very particularly preferably $\leq 0.8$ µm. The glass flakes may be covered with one or more layers. The glass flakes are preferably covered with coloured or colourless metal oxides, metal hydroxides, metal suboxides or metal oxynitrides. Suitable metal oxides are, in particular, $TiO_2$, $Fe_2O_3$, $Fe_3O_4$, $FeO(OH)$, $SnO_2$, $Cr_2O_3$, $ZrO_2$, $ZnO$, $CuO$, $NiO$, vanadium oxides and manganese oxides and other metal oxides, alone or in a mixture, in the same layer or in successive layers. Titanium suboxides and titanium nitrides are furthermore suitable for the coating.

Preferred coated glass-flake pigments have the following structure:

glass flake+$Fe_2O_3$ layer
glass flake+$SiO_2$ layer+$TiO_2$ layer
glass flake+$TiO_2$ layer
glass flake+$TiO_2$ layer+$SiO_2$ layer+$TiO_2$/$Fe_2O_3$ layer
glass flake+$TiO_2$/$Fe_2O_3$ layer+$SiO_2$ layer+$TiO_2$/$Fe_2O_3$ layer
glass flake+$TiO_2$ layer+$SiO_2$ layer+$Cr_2O_3$ layer
glass flake+$SiO_2$ layer+$Fe_2O_3$ layer
glass flake+$Cr_2O_3$ layer
glass flake+Ag
glass flake+Au
glass flake+$Fe_2O_3$ layer+$SiO_2$ layer+$TiO_2$/$Fe_2O_3$ layer
glass flake+$SiO_2$ layer+$TiO_2$ layer+$SiO_2$ layer+$TiO_2$ layer
glass flake+$SiO_2$ layer+$TiO_2$/$Fe_2O_3$ layer+$SiO_2$ layer+$TiO_2$/$Fe_2O_3$ layer
glass flake+$SiO_2$ layer+$Fe_2O_3$ layer+$SiO_2$ layer+$TiO_2$/$Fe_2O_3$ layer Instead of the outer metal-oxide layer, it is also possible to use a semitransparent layer of a metal. Suitable metals for this purpose are, for example, Cr, Ti, Mo, W, Al, Cu, Ag, Au or Ni.

In order to achieve specific colour effects, finely divided particles in the nanometre size range may additionally be incorporated into layers. Suitable for this purpose have proven to be, for example, finely divided $TiO_2$ or $ZnO$ or finely divided carbon (carbon black) having particle sizes in the range 10-250 nm. The light-scattering properties of such particles furthermore enable the gloss and hiding power to be influenced more specifically.

Particularly preferred glass flakes are $TiO_2$- and/or $Fe_2O_3$-coated flakes or glass flakes which initially have an $SiO_2$ coating and are subsequently coated with $TiO_2$ and/or $Fe_2O_3$. Suitable glass flakes can be produced as described, for example, in the patent literature EP 0 289 240 B1, WO 97/46624, WO 02/090448 A2, WO 03/006558 A2 and WO 2004/055119 A1.

The coated or uncoated glass flakes are preferably admixed with component B in amounts of 1-50% by weight, in particular 3-25% by weight and very particularly preferably 5-15% by weight. However, the respective composition of the pigment mixture according to the invention is dependent on the application medium to be pigmented and on the desired effect.

Component B comprises pearlescent pigments based on flake-form, trans-parent or semitransparent substrates comprising phyllosilicates, such as natural and synthetic mica, talc, sericite, kaolin or other silicate materials, and based on $SiO_2$ flakes, $Fe_2O_3$ flakes and $Al_2O_3$ flakes which are coated with coloured or colourless metal oxides, nitrides or suboxides, such as, for example, $TiO_2$, titanium suboxides, titanium oxynitrides, $Fe_2O_3$, $Fe_3O_4$, $FeO(OH)$, $SnO_2$, $Cr_2O_3$, $ZnO$, $ZrO_2$, CuO, pseudobrookite, NiO, manganese oxides and tungsten oxides and other metal oxides, alone or in a mixture, in the same layer or in successive layers. Pearlescent pigments of this type are known, for example, from the German patents and patent applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017 and P 38 42 330 and are commercially available from Merck KGaA, Darmstadt, Germany, for example under the trade name Iriodin®. Particularly preferred pigment preparations comprise $TiO_2$/mica, $Fe_2O_3$/mica and/or $TiO_2/Fe_2O_3$ mica pigments as component B.

Preference is furthermore given to $TiO_2$- and/or $Fe_2O_3$-coated $SiO_2$ flakes or $Al_2O_3$ flakes. The coating of the $SiO_2$ flakes with one or more metal oxides can be carried out, for example, as described in WO 93/08237 (wet-chemical coating) or DE-A 196 14 637 (CVD process). Preferred $SiO_2$ flakes are colourless, i.e. they comprise no colorants.

Component B may likewise comprise multilayered pigments as pearlescent pigment. Multilayered pigments of this type, in particular based on mica and $TiO_2$, are known, for example, from the German applications DE 196 18 563, DE 196 18 566, DE 196 18 569, DE 197 07 805, DE 197 07 806, DE 197 46 067 and generally have alternating high- and low-refractive-index layers, preferably comprising metal oxides. Preferred multilayered pigments comprise up to 7 layers, preferably 3, 5 or 7 layers.

Component B may also consist of a mixture of various pearlescent pigments. It is possible to mix multilayered pigments with both monocoated pearlescent pigments and also pearlescent pigments based on different substrates. However, component B preferably consists only of one pearlescent pigment, in particular a monocoated mica flake.

The pearlescent pigments of component B are preferably based on mica flakes, $Al_2O_3$ flakes, $Fe_2O_3$ flakes and $SiO_2$ flakes, which generally have a thickness of between 0.3 and 5 µm, in particular between 0.4 and 2.0 µm. The size in the two other dimensions is usually between 1 and 250 µm, preferably between 2 and 100 µm and in particular between 5 and 60 µm.

Component B may also comprise coated or uncoated BiOCl pigments. Pigments of this type, which are particularly suitable for offset printing, are commercially available, for example from Engelhard under the name Mearlite® Ultra Fine OFS, and from Merck KGaA under the name Biflair®. The commercially available BiOCl pigments have particle sizes of 1-50 µm. For the pigment mixture according to the invention, BiOCl pigments having particle sizes of 5-20 µm, preferably of <15 µm, are particularly suitable.

Component A and component B preferably each have particle sizes in the range 5-200 µm.

In order to increase the light, water and weather stability, it is frequently advisable, depending on the area of application, to subject the pigments of component A and/or B to post-coating or post-treatment. Suitable postcoatings or post-treatments are, for example, the processes described in German Patent 22 15 191, DE-A 31 51 354, DE-A 32 35 017 or DE-A 33 34 598. This post-coating further increases the chemical stability or simplifies handling of the pigment, in particular incorporation into various media. In order to improve the wettability, dispersibility and/or compatibility with the application media, functional coatings of $Al_2O_3$ or $ZrO_2$ or mixtures or mixed phases thereof can be applied to the pigment surface. Furthermore, organic or combined organic/inorganic post-coatings are possible, for example with silanes, as described, for example, in EP 0090259, EP 0 634 459, WO 99/57204, WO 96/32446, WO 99/57204, U.S. Pat. No. 5,759,255, U.S. Pat. No. 5,571,851, WO 01/92425 or in J. J. Ponjeé, Philips Technical Review, Vol. 44, No. 3, 81 ff. and P. H. Harding, J. C. Berg, J. Adhesion Sci. Technol., Vol. 11, No. 4, pp. 471-493.

The additionally applied substances make up only about 0.1 to 5% by weight, preferably 0.5 to 3.0% by weight, of the pigments of component A and/or B.

The pigment mixture according to the invention is relatively simple and easy to handle. The desired amount of coated or uncoated glass flakes is added to component B. The mixing is carried out by means of conventional mixing units, such as, for example, drum hoop mixers, paddle mixers, tumble mixers, Lödige mixers. The finished pigment mixture can then be incorporated into the application system by simple stirring-in. Complex grinding and dispersal of the pigments is not necessary.

The pigment mixture according to the invention can be used, for example, for the pigmenting of surface coatings, powder coatings, industrial coatings, automobile paints, inks, printing inks, plastics, plastic films, agricultural sheeting, seed coating, button pastes, for finishing foods, medicament coatings, dragees and tablets. The concentration of the pigment mixture in the application system to be pigmented is generally between 0.1 and 70% by weight, preferably between 0.1 and 50% by weight and in particular between 1.0 and 10% by weight, based on the total solids content of the system. It is generally dependent on the specific application.

Owing to its hiding power and very strong glitter effect, the pigment mixture according to the invention is preferably suitable for printing inks, in particular for screen printing, gravure printing, flexographic printing, offset printing, overprint varnishing, pad printing, halftone printing, for paper coating, for knife coating and air-knife coating.

The matching of the properties of print material, printing ink and pigment mixture according to the invention is dependent on the respective printing process.

The pigment mixture is generally incorporated into the printing ink in amounts of 2-35% by weight, preferably 5-25% by weight and in particular 8-20% by weight. Offset printing inks may comprise up to 40% by weight or more of the pigment mixture.

The printing inks comprising the pigment mixture according to the invention exhibit purer hues, more intense gloss and can be printed better owing to the good viscosity values.

In offset printing inks, very finely divided pigments are preferably employed, in particular pigments having particle sizes <15 µm. Particular preference is given to offset printing inks comprising 1-30% by weight of component B and 1-15% by weight of component A. The mixing ratio of components A and B is in the range from 10:90 to 50:50. The pigment mixture according to the invention is preferably present in the offset printing ink in a maximum amount of 30% by weight. Suitable binders are, for example, gloss overprint varnish or uncoloured bronze varnish, for example from Geb. Schmidt, K+E or Jänecke und Schneemann.

Printing inks for screen printing preferably comprise 1-15% by weight of component B, preferably pearlescent pigments, and 1-7.5% of component A. The mixing ratio of components A and B is in the range from 10:90 to 50:50. The mixture of components A and B is preferably present in the screen-printing ink in a maximum amount of 15% by weight. Suitable binders are, for example, Helizarin MT from BASF AG.

Printing inks for rotary screen printing preferably comprise 1-13% by weight of component B, preferably pearlescent pigments, and 1-6.5% of component A. The mixing ratio of components A and B is in the range from 10:90 to 50:50. The mixture of components A and B is preferably pre-sent in the rotary-printing ink in a maximum amount of 15% by weight. Suitable binders are, for example, Tubiscreen MET-H from CHT.

The pigment mixture according to the invention is likewise very highly suitable for paper coating. The coating preferably comprises 1-7% by weight of component B, preferably pearlescent pigments, and 1-3.5% of component A. The mixing ratio of components A and B is in the range from 10:90 to 50:50. The mixture of components A and B is preferably pre-sent in the coating in a maximum amount of 7% by weight. Suitable binders are, for example, Pröll Aqua Jet from Pröll.

In the preparation of a gravure printing ink, 1-30% by weight of component B, preferably pearlescent pigments, and 1-15% by weight of component A are stirred into the finished printing ink. The mixing ratio of components A and B is in the range from 10:90 to 50:50. The mixture of components A and B is preferably present in the gravure printing ink in a maximum amount of 30%.

Printing inks for flexographic printing preferably comprise 1-30% by weight of component B, in particular pearlescent pigments, and 1-15% by weight of component A. The mixing ratio of components A and B is in the range from 10:90 to 50:50. The mixture of components A and B is preferably present in the flexographic printing ink in a maximum amount of 30% by weight. Suitable binders are, for example, Weilburger Senolith primer flexographic printing binder from Weilburger Graphics GmbH.

All print materials known to the person skilled in the art, in particular textiles, paper and films, can be printed very well with the pigment mixture according to the invention.

Plastics comprising the pigment mixture according to the invention in amounts of 0.01 to 50% by weight, in particular 0.1 to 7.0% by weight, are frequently distinguished by a particular colour effect, but also by a sparkle effect.

In the paints sector, in particular in automobile paints, the pigment mixture is employed in amounts of 0.1-10% by weight, preferably 1 to 3% by weight, also for three-coat structures. The pigment mixture according to the invention has the advantage in paints that the target effect is achieved by a single-coat finish (one-coat system or base coat in two-coat structure). Compared with finishes which comprise only component B instead of the pigment mixture according to the invention, finishes comprising the pigment mixture according to the invention exhibit a clearer depth effect and a glitter effect.

In the pigmenting of binder systems, for example for inks and printing inks for gravure printing, offset printing or screen printing, rotary screen printing or as precursor of printing inks, for example in the form of highly pigmented pastes, granules, pellets, etc., pigment mixtures having spherical particles, for example solid or hollow glass beads, polymer beads, $SiO_2$ beads, and/or having spherical colorants, such as, for example, $TiO_2$, carbon black, chromium oxide, iron oxide, and organic coloured pigments, have proven particularly suitable.

Precursors of printing inks, for example in granule form, as pellets, briquettes, etc., comprise up to 98% by weight of the pigment mixture according to the invention in addition to the binder and additives.

The pigment mixture according to the invention is furthermore suitable for pigment pastes and for the preparation of pastes and dry preparations, such as, for example, granules, pellets, briquettes, sausages, beads, etc.

The invention thus also relates to formulations comprising the pigment mixture according to the invention.

The following examples are intended to explain the invention, but without restricting it.

EXAMPLES

I. Preparation of the Pigment Mixture

The desired amount of Ronastar® Noble Sparks (pearlescent pigment based on glass flakes having a particle size of 20-200 µm coated with $SiO_2$ and $TiO_2$ from Merck KGaA) is added to Iriodin® 103 (pearlescent pigment based on mica having a particle size of 10-60 µm coated with $TiO_2$ from Merck KGaA) and mixed using a drum hoop mixer.

Example 1

The following pigment mixtures are prepared:

Example 1a

Ronastar® Noble Sparks/Iriodin® 103 in the ratio 50:50.

Example 1b

Ronastar® Noble Sparks/Iriodin® 103 in the ratio 25:75.

Example 1c

Ronastar® Noble Sparks/Iriodin® 103 in the ratio 10:90.

Example 1d $Fe_2O_3$-coated glass flakes+Iriodin® 103 in the ratio 50:50.

Example 1e $TiO_2/SiO_2/TiO_2$-coated glass flakes+Iriodin® 103 in the ratio 25:75.

Example 1f $TiO_2$-coated glass flakes+Iriodin® 103 in the ratio 10:90.

Example 1g $Fe_2O_3$- and $SiO_2$-coated glass flakes+Iriodin® 103 in the ratio 50:50.

Example 1h $SiO_2/TiO_2/SiO_2/TiO_2$-coated multilayered pigments based on glass flakes+Iriodin® 103 in the ratio 10:90.

II. Gloss Measurements

A pigment mixture consisting of pearlescent pigments based on mica flakes and coated glass flakes exhibits significantly higher gloss values (measured by the Gardner method, DIN 67530, ISO 2813, ASTM D 523) than the coated glass flake alone:

| Pigment mixture | Angle 20° | Angle 60° |
|---|---|---|
| Ronastar ® Noble Sparks | 3.9 | 12.6 |
| Iriodin ® 103 | 2.8 | 8.9 |
| 50:50 mixture | 10.7 | 44.1 |

-continued

| Pigment mixture | Angle 20° | Angle 60° |
|---|---|---|
| (Ronastar ® Noble Sparks/Iriodin ® 103) 25:75 mixture | 6.2 | 25.9 |
| (Ronastar ® Noble Sparks/Iriodin ® 103) 10:90 mixture | 5.8 | 22.1 |
| (Ronastar ® Noble Sparks/Iriodin ® 103) | | |

The addition of Ronastar® Noble Sparks increases the gloss effect of Iriodin® 103 well beyond the effect to be expected (gloss booster effect).

III. Use Examples

Example A1

Screen Printing

For the preparation of 1 kg of printing ink, 850 g of binder (Helizarin MT from BASF AG) and 150 g of pigment mixture consisting of 120 g of Iriodin® 123 (TiO$_2$/mica pigment having a particle size of 5-20 μm from Merck KGaA) and 30 g of Ronastar® Noble Sparks are mixed at about 800-1200 rpm using a propeller stirrer and then printed.

The print product shows a very pronounced glitter effect on paper and textile and, through the addition of Ronastar® Noble Sparks, the brightness and gloss are doubled compared with pure Iriodin® 123.

Example A2

Rotary Screen Printing

For the preparation of 1 kg of printing ink, 880 g of binder (Tubiscreen MET-H from CHT) and 120 g of pigment mixture consisting of 100 g of Iriodin® 225 (TiO$_2$/mica pigment having a particle size of 10-60 μm from Merck KGaA) and 20 g of Ronastar® Noble Sparks are mixed at about 800-1200 rpm using a propeller stirrer and then printed.

On textiles, the print shows very high gloss with a very pronounced glitter effect.

Example A3

Paper Coating

For the preparation of 1 kg of printing ink, 920 g of Pröll Aqua Jet from Pröll and 80 g of pigment mixture consisting of 70 g of Iriodin® 100 (TiO$_2$/mica pigment having a particle size of 10-60 μm from Merck KGaA) and 10 g of Ronastar® Noble Sparks are mixed at about 800-1200 rpm using a propeller stirrer and then printed.

The coated paper shows a very bright and pronounced glitter effect.

Example A4

Gravure Printing

For the preparation of 1 kg of printing ink, 750 g of Sicpa 50.36 rotogravure printing binder from Sicpa and 250 g of pigment mixture consisting of 200 g of Iriodin® 305 Solar Gold (multilayered pigment based on mica coated with pseudobrookite having a particle size of 10-60 μm from Merck KGaA) and 50 g of Ronastar® Noble Sparks are mixed at about 800-1200 rpm using a propeller stirrer and then printed.

The print product shows a very pronounced glitter effect on paper and textile and, through the addition of Ronastar® Noble Sparks, the brightness and gloss are doubled compared with pure Iriodin® 305.

Example A5

Flexographic Printing

For the preparation of 1 kg of printing ink, 700 g of Weilburger Senolith® primer flexographic printing binder from Weilburger Graphics GmbH and 300 g of pigment mixture consisting of 200 g of Iriodin® 225 and 100 g of Ronastar® Noble Sparks are mixed at about 800-1200 rpm using a propeller stirrer and then printed.

The print product shows a very pronounced glitter effect on paper and textile and, through the addition of Ronastar® Noble Sparks, the brightness and gloss are doubled compared with pure Iriodin® 225.

Example A6

Offset Printing

For the preparation of 1 kg of printing ink (700 g of gloss overprint varnish binder from Gebr. Schmidt), 150 g of pigment mixture consisting of 150 g of Iriodin® 100 (TiO$_2$/mica pigment having a particle size of 10-60 μm from Merck KGaA) and 150 g of Ronastar® Noble Sparks are stirred in at about 800-1200 rpm using a propeller stirrer and then printed.

The printed paper shows high gloss and a very fine and intense sparkle effect.

Example A7

Offset Printing

For the preparation of 1 kg of printing ink (700 g of gloss overprint varnish binder from Gebr. Schmidt), 150 g of pigment mixture consisting of 150 g of Biflair® (BiOCl pigment having a particle size of 7-15 μm from Merck KGaA) and 150 g of Ronastar® Noble Sparks are stirred in at about 800-1200 rpm using a propeller stirrer and then printed.

The printed paper shows an extremely high silky gloss and a very fine and intense sparkle effect.

Example 3

Plastic

A 1:1 mixture of in each case a) 1% of SiO$_2$ flakes having a particle size of 5-40 μm, coated with TiO$_2$, b) 1% of Iriodin® 103, c) 1:1 mixture of Ronastar® Noble Sparks/Iriodin® 103, is stirred into plastic granules comprising Stamylan PPH10 polypropylene PP (DSM) or polystyrene 143 E (BASF). The pigmented granules are subsequently converted into plates (size 9×6 cm) in an injection-moulding machine.

On use of the pigments under a) and b), plastic plates of high gloss are obtained. The plastic plates from Example c) exhibit higher gloss and in addition a very pronounced glitter effect.

The invention claimed is:

1. Pigment mixture comprising at least two components, where
   component A comprises mono- or polycoated glass flakes which glass flakes initially have a $SiO_2$ coating on their surface and are subsequently coated with one or more metal oxides, and
   component B comprises coated or uncoated BiOCl pigments or pearlescent pigments based on phyllosilicates, $SiO_2$ flakes, $Fe_2O_3$ flakes or $Al_2O_3$ flakes.

2. Pigment mixture according to claim 1, wherein component A and component B each have particle sizes of 5-200 μm.

3. Pigment mixture according to claim 1, wherein component A and component B are mixed in the ratio 10:90 to 50:50.

4. Pigment mixture according to claim 1, wherein the glass flakes are completely or partly coated with $TiO_2$ and/or $Fe_2O_3$.

5. Pigment mixture according to claim 1, wherein the glass flakes initially have a $SiO_2$ coating on the surface and are subsequently coated with one to three metal oxides.

6. Pigment mixture according to claim 1, wherein the pearlescent pigment based on phyllosilicates, $SiO_2$ flakes, $Fe_2O_3$ flakes or $Al_2O_3$ flakes is coated with one or more metal oxides, metal hydroxides, metal suboxides and/or metal oxynitrides.

7. Pigment mixture according to claim 1, wherein component B is a pearlescent pigment based on phyllosilicates which is coated with $TiO_2$ and/or $Fe_2O_3$.

8. Pigment mixture according to claim 1, wherein the phyllosilicate is natural or synthetic mica.

9. Pigment mixture according to claim 1, wherein the mixture comprises up to 50% by weight of component A, based on components A and B in the mixture.

10. A product selected from the group consisting of inks, surface coatings, powder coatings, industrial coatings, automobile paints, printing inks, plastics, plastic films, agricultural sheeting, button pastes, colouring seed, cosmetic formulations, foods, pastes, dry preparations and pigment pastes, comprising a pigment mixture according to claim 1.

11. A method for screen printing, rotary screen printing, gravure printing, flexographic printing, offset printing, overprint varnishing, pad printing, halftone printing, for knife coating and air-knife coating and for paper coating, which comprises printing or coating with a pigment mixture according to claim 1 or with a composition comprising said pigment mixture.

12. Formulation comprising a pigment mixture according to claim 1.

13. Pigment mixture comprising at least two components A and B, where component A comprises coated glass flakes wherein the glass flakes initially have an $SiO_2$ coating on the surface and are subsequently coated with one or more metal oxides,
   and
   component B comprises coated or uncoated BiOCl pigments or pearlescent pigments based on phyllosilicates, $SiO_2$ flakes, $Fe_2O_3$ flakes or $Al_2O_3$ flakes,
   wherein component A and component B each have particle sizes of 5-200, and
   wherein component A and component B are mixed in the ratio 10:90 to 50:50.

14. Pigment mixture according to claim 13, wherein the glass flakes are completely or partly coated with $TiO_2$ and/or $Fe_2O_3$.

15. Pigment mixture according to claim 13, wherein the pearlescent pigment based on phyllosilicates, $SiO_2$ flakes, $Fe_2O_3$ flakes or $Al_2O_3$ flakes is coated with one or more metal oxides, metal hydroxides, metal suboxides and/or metal oxynitrides.

16. Pigment mixture according to claim 13, wherein component B is a pearlescent pigment based on phyllosilicates which is coated with $TiO_2$ and/or $Fe_2O_3$.

17. Pigment mixture according to claim 13, wherein the phyllosilicate is natural or synthetic mica.

18. Pigment mixture according to claim 13, wherein the mixture comprises up to 50% by weight of component A, based on components A and B in the mixture.

19. A product selected from the group consisting of inks, surface coatings, powder coatings, industrial coatings, automobile paints, printing inks, plastics, plastic films, agricultural sheeting, button pastes, colouring seed, cosmetic formulations, foods, pastes, dry preparations and pigment pastes, comprising a pigment mixture according to claim 13.

20. A method for screen printing, rotary screen printing, gravure printing, flexographic printing, offset printing, overprint varnishing, pad printing, halftone printing, for knife coating and air-knife coating and for paper coating, which comprises printing or coating with a pigment mixture according to claim 13 or with a composition comprising said pigment mixture.

* * * * *